US012611246B2

(12) United States Patent
Tschudy et al.

(10) Patent No.: US 12,611,246 B2
(45) Date of Patent: Apr. 28, 2026

(54) END EFFECTOR DRIVE MECHANISMS FOR SURGICAL INSTRUMENTS SUCH AS FOR USE IN ROBOTIC SURGICAL SYSTEMS

(71) Applicant: Covidien LP, Mansfield, MA (US)

(72) Inventors: Christopher T. Tschudy, Arvada, CO (US); Dylan R. Kingsley, Broomfield, CO (US); Sara A. Malang, Longmont, CO (US); James H. Bodmer, Longmont, CO (US); Tony G. Moua, Broomfield, CO (US); Andrew W. Zeccola, Allston, MA (US); Curtis M. Siebenaller, Frederick, CO (US); Haralambos P. Apostolopoulos, Highlands Ranch, CO (US); Russell W. Holbrook, Longmont, CO (US); William R. Whitney, Boulder, CO (US); Jason G. Weihe, Boulder, CO (US); Zachary S. Heiliger, Nederland, CO (US)

(73) Assignee: Covidien LP, Mansfield, MA (US)

(*) Notice: Subject to any disclaimer, the term of this patent is extended or adjusted under 35 U.S.C. 154(b) by 1137 days.

(21) Appl. No.: 17/403,491

(22) Filed: Aug. 16, 2021

(65) Prior Publication Data

US 2023/0047599 A1     Feb. 16, 2023

(51) Int. Cl.
A61B 18/14     (2006.01)
A61B 17/00     (2006.01)
(Continued)

(52) U.S. Cl.
CPC .............................. A61B 18/1445 (2013.01); A61B 2017/00075 (2013.01); A61B 2017/00367 (2013.01);
(Continued)

(58) Field of Classification Search
CPC . A61B 18/1445; A61B 18/1442; A61B 34/77; A61B 34/76; A61B 34/30; A61B 34/70; A61B 34/37
See application file for complete search history.

(56) References Cited

U.S. PATENT DOCUMENTS

| | | | |
|---|---|---|---|
| 5,752,973 A | 5/1998 | Kieturakis | |
| 5,792,135 A | 8/1998 | Madhani et al. | |
| | (Continued) | | |

OTHER PUBLICATIONS

Extended European Search Report issued in corresponding European Application No. 22190423.8 dated Jan. 16, 2023, 15 pages.
(Continued)

*Primary Examiner* — Ronald Hupczey, Jr.
(74) *Attorney, Agent, or Firm* — Carter, DeLuca & Farrell LLP

(57) ABSTRACT

A robotic system includes an electrosurgical instrument having an instrument housing having a shaft with an end effector assembly and first and second jaw members attached thereto movable to grasp tissue. An input is operably coupled to the instrument housing and is configured to move the jaw members. A handle is remotely disposed relative to the instrument housing and is configured to communicate with the input for controlling the jaw members, the handle having a lever configured to cooperate with the input to control the jaw members relative to movement of the lever. The lever moves between a homing position and a first position correlating to the jaw members closing with a pressure therebetween in the range of about 0.1 kg/cm$^2$ to about 2 kg/cm$^2$. The lever further movable to a seal position correlating to the jaw members closing about tissue with a pressure between about 3 kg/cm$^2$ to about 16 kg/cm$^2$ for sealing.

15 Claims, 8 Drawing Sheets

(51) Int. Cl.
    *A61B 17/29* (2006.01)
    *A61B 18/00* (2006.01)
    *A61B 34/30* (2016.01)

(52) U.S. Cl.
    CPC ................ *A61B 2017/2912* (2013.01); *A61B 2018/0063* (2013.01); *A61B 2018/00773* (2013.01); *A61B 34/30* (2016.02)

(56) References Cited

U.S. PATENT DOCUMENTS

| | | | |
|---|---|---|---|
| 5,848,986 A | 12/1998 | Lundquist et al. | |
| 6,731,988 B1* | 5/2004 | Green | A61B 34/35 348/E13.016 |
| 6,817,974 B2 | 11/2004 | Cooper et al. | |
| 7,799,028 B2 | 9/2010 | Schechter et al. | |
| 7,861,906 B2 | 1/2011 | Doll et al. | |
| 7,918,230 B2 | 4/2011 | Whitman et al. | |
| 8,579,176 B2 | 11/2013 | Smith et al. | |
| 9,055,961 B2 | 6/2015 | Manzo et al. | |
| 9,474,569 B2 | 10/2016 | Manzo et al. | |
| 10,731,740 B1 | 8/2020 | Cui et al. | |
| 10,945,797 B2 | 3/2021 | Anglese | |
| 11,058,504 B2 | 7/2021 | Blanco et al. | |
| 2002/0099371 A1 | 7/2002 | Schulze et al. | |
| 2002/0177842 A1 | 11/2002 | Weiss | |
| 2003/0125734 A1 | 7/2003 | Mollenauer | |
| 2003/0208186 A1 | 11/2003 | Moreyra | |
| 2006/0022015 A1 | 2/2006 | Shelton et al. | |
| 2006/0025811 A1 | 2/2006 | Shelton | |
| 2006/0161138 A1 | 7/2006 | Orban, III | |
| 2007/0233052 A1 | 10/2007 | Brock | |
| 2008/0015631 A1 | 1/2008 | Lee et al. | |
| 2008/0134812 A1 | 6/2008 | Murata | |
| 2010/0274265 A1 | 10/2010 | Wingardner et al. | |
| 2010/0292691 A1 | 11/2010 | Brogna | |
| 2011/0077648 A1* | 3/2011 | Lee | A61B 18/1445 606/51 |

| | | | |
|---|---|---|---|
| 2011/0118707 A1 | 5/2011 | Burbank | |
| 2011/0118708 A1 | 5/2011 | Burbank et al. | |
| 2011/0118709 A1 | 5/2011 | Burbank | |
| 2011/0118754 A1 | 5/2011 | Dachs, II | |
| 2013/0013824 A1 | 1/2013 | Graefe | |
| 2013/0103050 A1* | 4/2013 | Richmond | A61B 17/285 606/130 |
| 2013/0123783 A1 | 5/2013 | Marczyk et al. | |
| 2014/0074091 A1* | 3/2014 | Arya | A61B 18/1445 606/51 |
| 2014/0107646 A1* | 4/2014 | Garrison | A61B 18/1445 606/48 |
| 2014/0195048 A1 | 7/2014 | Moll et al. | |
| 2014/0276723 A1 | 9/2014 | Parihar et al. | |
| 2017/0042560 A1 | 2/2017 | Lee et al. | |
| 2017/0150975 A1 | 6/2017 | Bozung | |
| 2017/0265951 A1 | 9/2017 | Grover et al. | |
| 2017/0273749 A1 | 9/2017 | Grover et al. | |
| 2017/0319228 A1 | 11/2017 | Worrell et al. | |
| 2017/0365923 A1 | 12/2017 | Schmutzler et al. | |
| 2018/0028271 A1 | 2/2018 | Rockrohr | |
| 2018/0071037 A1 | 3/2018 | Grover et al. | |
| 2019/0008600 A1 | 1/2019 | Pedros et al. | |
| 2019/0099227 A1 | 4/2019 | Rockrohr | |
| 2019/0274769 A1 | 9/2019 | Perdue et al. | |
| 2020/0237453 A1 | 7/2020 | Anglese | |
| 2020/0237455 A1 | 7/2020 | Anglese | |
| 2020/0246058 A1 | 8/2020 | Traina | |
| 2020/0253676 A1 | 8/2020 | Traina | |
| 2020/0253678 A1 | 8/2020 | Hulford et al. | |
| 2020/0261166 A1 | 8/2020 | Anglese | |
| 2020/0261167 A1 | 8/2020 | Anglese | |
| 2020/0261168 A1 | 8/2020 | Anglese | |
| 2020/0289191 A1 | 9/2020 | Soni | |

OTHER PUBLICATIONS

Extended European Search Report issued in corresponding European Application No. 20154024.2 dated Jun. 26, 2020, 9 pages.

* cited by examiner

END EFFECTOR DRIVE MECHANISMS FOR SURGICAL INSTRUMENTS SUCH AS FOR USE IN ROBOTIC SURGICAL SYSTEMS

FIELD

The present disclosure relates to surgical instruments and, more specifically, to end effector drive mechanisms for surgical instruments such as for use in robotic surgical systems.

BACKGROUND

Robotic surgical systems are increasingly utilized in various different surgical procedures. Some robotic surgical systems include a console supporting a robotic arm. One or more different surgical instruments may be configured for use with the robotic surgical system and selectively mountable to the robotic arm. The robotic arm provides one or more inputs to the mounted surgical instrument to enable operation of the mounted surgical instrument.

A surgical forceps, one type of instrument capable of being utilized with a robotic surgical system, relies on mechanical action between its jaw members to grasp, clamp, and constrict tissue. Electrosurgical forceps utilize both mechanical clamping action and energy to heat tissue to treat, e.g., coagulate, cauterize, or seal, tissue. Typically, once tissue is treated, the tissue is severed using a cutting element. Accordingly, electrosurgical forceps are designed to incorporate a cutting element to effectively sever treated tissue. Alternatively, energy-based, e.g., thermal, electrical, ultrasonic, etc., cutting mechanisms may be implemented.

With traditional surgical instrumentation, e.g., open and endoscopic surgical instrumentation, the surgeon is typically able to feel or otherwise sense direct feedback from the end effector relating to the size of the tissue between the jaw members as well as the force being applied during manipulation and sealing. With robotic instrumentation, haptic feedback may be lost or sacrificed for ease of use to offset among other things, surgical fatigue.

SUMMARY

As used herein, the term "distal" refers to the portion that is being described which is farther from an operator (whether a human surgeon or a surgical robot), while the term "proximal" refers to the portion that is being described which is closer to the operator. The terms "about," "substantially," and the like, as utilized herein, are meant to account for manufacturing, material, environmental, use, and/or measurement tolerances and variations, and in any event may encompass differences of up to 10%. Further, to the extent consistent, any of the aspects described herein may be used in conjunction with any or all of the other aspects described herein.

Provided in accordance with aspects of the present disclosure is a robotic surgical system including an electrosurgical instrument including an instrument housing having a shaft extending therefrom. An end effector assembly is disposed at a distal end of the shaft and includes first and second jaw members movable between a first position wherein one or both of the jaw members is spaced relative to the other of the jaw members and a second position wherein the first and second jaw members cooperate to grasp tissue. An input is operably coupled to the instrument housing and is configured to move the jaw members between the first and second positions. One or more handles is remotely disposed relative to the instrument housing and is configured to communicate with the input for controlling the jaw members. The handle includes a housing having a lever operably coupled thereto, the lever, in turn, is configured to cooperate with the input to control the movement of the jaw members relative to movement of the lever. The lever is moveable between a homing position wherein the lever is spaced relative to the housing and the correlating jaw members are disposed in the first position and a grasp position wherein the lever is closer to the housing and the correlating jaw members are closed about tissue with a pressure between the jaw members in the range of about 0.1 kg/cm$^2$ to about 2 kg/cm$^2$. The lever is also movable between the grasp position and a seal position wherein the lever is closer to the housing and the correlating jaw members are closed about tissue with a pressure between the jaw members in the range of about 3 kg/cm$^2$ to about 16 kg/cm$^2$ for sealing tissue between the jaw members upon activation of electrosurgical energy.

In aspects according to the present disclosure, the housing of the one handle includes a cavity defined therein configured to house one or more components therein configured to operably connect to the input such that movement of the lever relative to the housing correlates to movement of the jaw members between the first and second positions.

In aspects according to the present disclosure, the correlation of movement of the lever and the jaw members is linear. In other aspects according to the present disclosure, the correlation of movement of the lever and the jaw members is non-linear.

In aspects according to the present disclosure, the combination of components disposed in the cavity correlate the actuation force of the lever to the applied closure pressure between the jaw members with tissue engaged therebetween. In aspects according to the present disclosure, the combination of components disposed in the cavity include levers, gears, linkages, and springs.

Provided in accordance with aspects of the present disclosure is a robotic surgical system including an electrosurgical instrument including an instrument housing having a shaft extending therefrom. An end effector assembly is disposed at a distal end of the shaft and includes first and second jaw members movable between a first position wherein one or both of the jaw members is spaced relative to the other of the jaw members and a second position wherein the first and second jaw members cooperate to grasp tissue. An input is operably coupled to the instrument housing and is configured to move the jaw members between the first and second positions. One or more handles is remotely disposed relative to the instrument housing and configured to communicate with the input for controlling the jaw members. The handle includes a housing having a lever operably coupled thereto. The lever, upon movement thereof, cooperates with the input to impart movement of the jaw members between the first and second positions wherein initial movement of the lever from an unactuated position to a first position imparts movement to the jaw members with a closure pressure within the range of about 0.1 kg/cm$^2$ to about 2 kg/cm$^2$ and wherein subsequent movement of the lever beyond the first position imparts movement to the jaw members with a closure pressure within the range of about 3 kg/cm$^2$ to about 16 kg/cm$^2$.

In aspects according to the present disclosure, the housing of the handle includes a cavity defined therein configured to house one or more components therein configured to operably connect to the input such that movement of the lever relative to the housing correlates to movement of the jaw members between the first and second positions.

In aspects according to the present disclosure, the correlation of movement of the lever and the jaw members is linear. In other aspects according to the present disclosure, the correlation of movement of the lever and the jaw members is non-linear.

In aspects according to the present disclosure, the combination of components disposed in the cavity correlate the actuation force of the lever to the applied pressure between the jaw members with tissue engaged therebetween. In other aspects according to the present disclosure, the combination of components disposed in the cavity include levers, gears, linkages, and springs.

In aspects according to the present disclosure, the system further includes a tactile, visual and/or audible indicator operably associated with the lever configured to alert the user when the lever is moved beyond the first position.

Provided in accordance with aspects of the present disclosure is a robotic surgical system including an electrosurgical instrument including an instrument housing having a shaft extending therefrom. An end effector assembly is disposed at a distal end of the shaft and includes first and second jaw members movable between a first position wherein one or both of the jaw members is spaced relative to the other of the jaw members and a second position wherein the first and second jaw members cooperate to grasp tissue. An input is operably coupled to the instrument housing and is configured to move the jaw members between the first and second positions. One or more handles is remotely disposed relative to the instrument housing and configured to communicate with the input for controlling the jaw members. The handle includes: a housing having a lever operably coupled thereto; and a switch operably disposed on one or both of the levers or the housing. The switch is moveable between a first position where the lever, upon movement thereof, cooperates with the input to impart movement to the jaw members between the first and second positions with a closure pressure within the range of about 0.1 kg/cm² to about 2 kg/cm² and a second position wherein movement of the lever imparts movement to the jaw members with a closure pressure within the range of about 3 kg/cm² to about 16 kg/cm².

In aspects according to the present disclosure, movement of the switch to the second position configures the jaw members for electrosurgical activation. In other aspects according to the present disclosure, when the switch is disposed in the first position, electrosurgical energy is deactivated.

In aspects according to the present disclosure, the system further includes a tactile, visual and/or audible indicator of the closure pressure between the jaw members.

BRIEF DESCRIPTION OF THE DRAWINGS

Various aspects and features of the present disclosure are described hereinbelow with reference to the drawings wherein.

DETAILED DESCRIPTION

Figure 1:
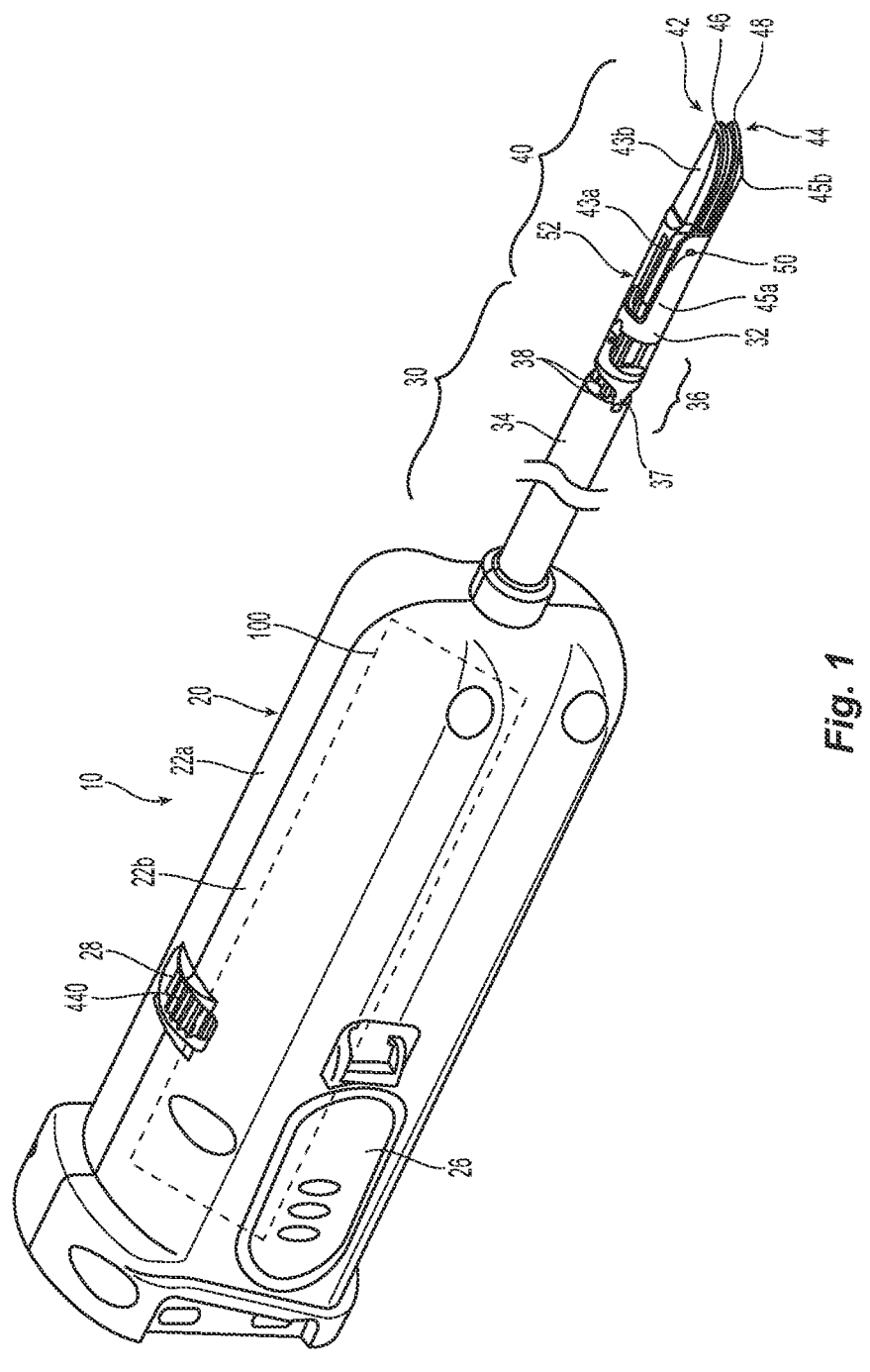
FIG. 1 is a perspective view of a surgical instrument in accordance with the present disclosure configured for mounting on a robotic arm of a robotic surgical system.
Figure 2:
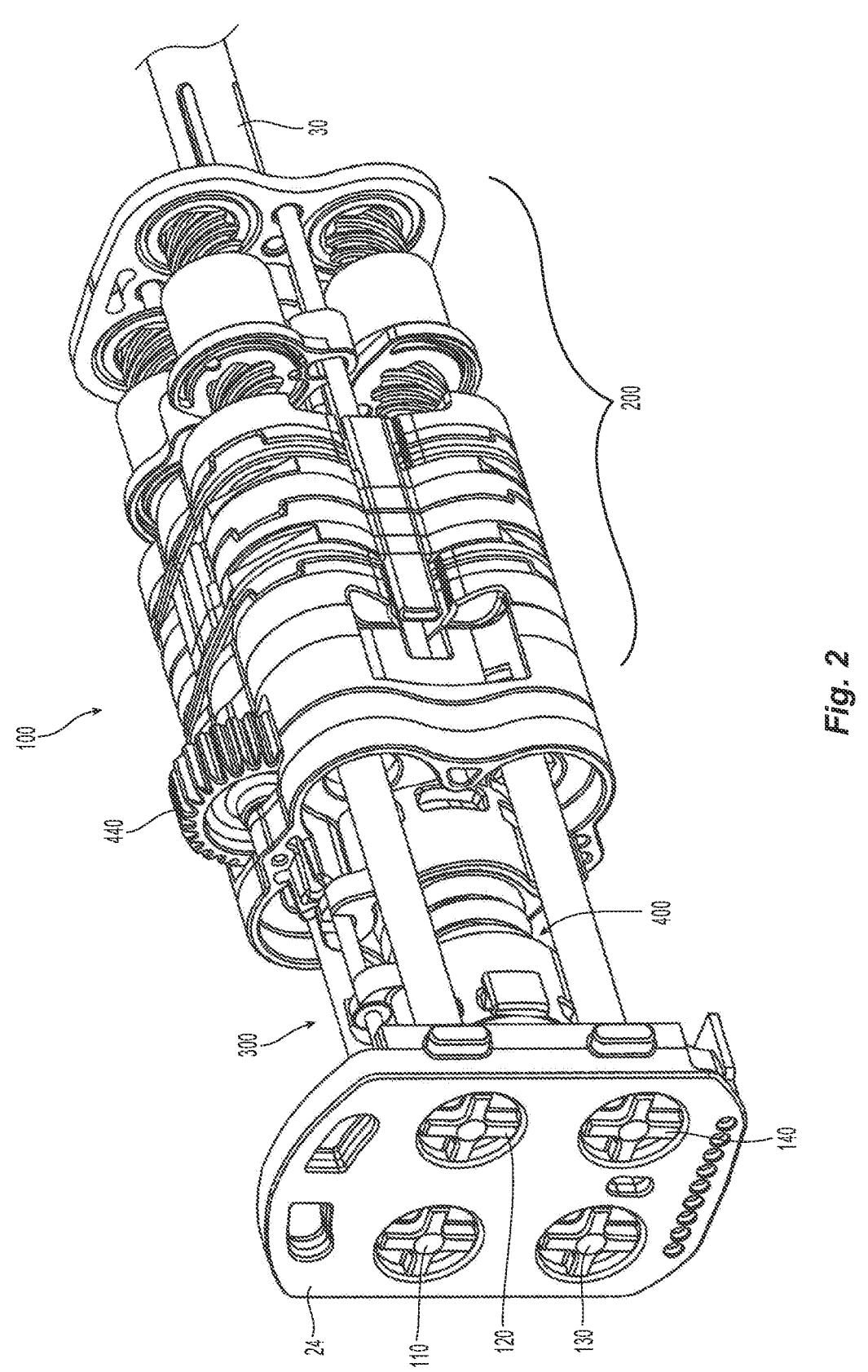
FIG. 2 is a rear perspective view of a proximal portion of the surgical instrument of FIG. 1 with an outer housing removed.
Figure 3:
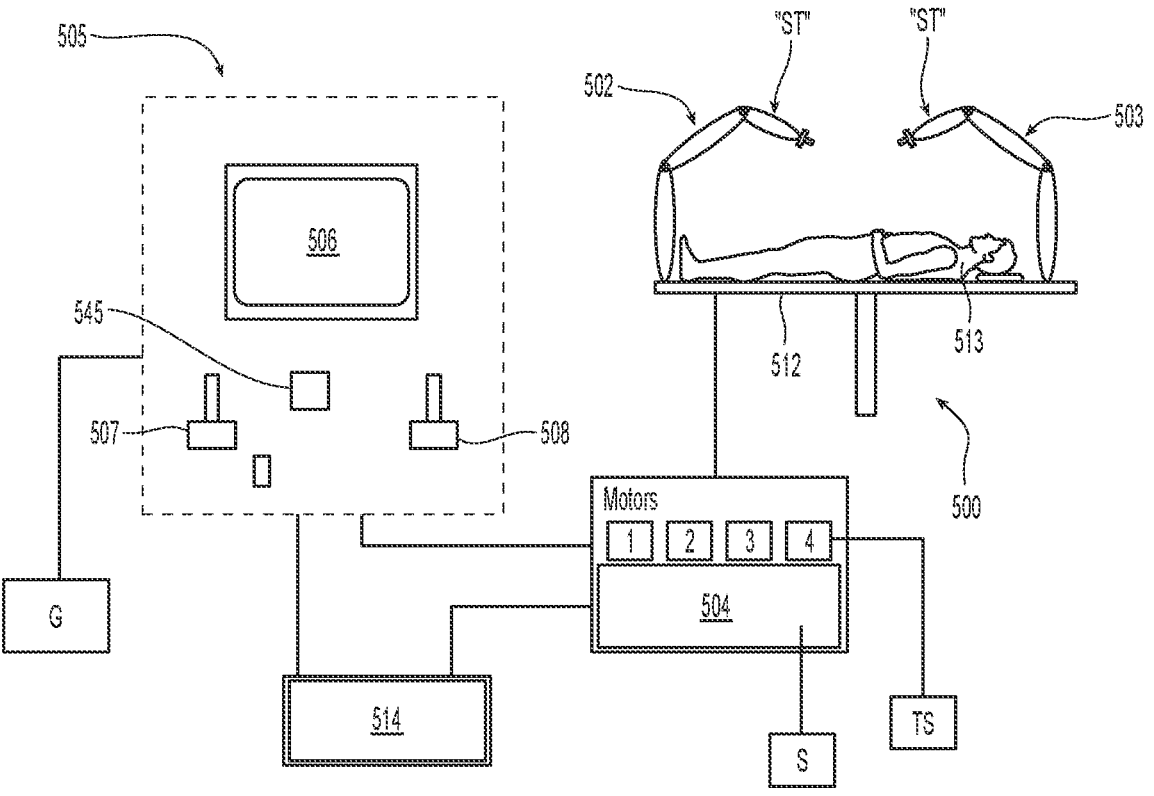
FIG. 3 is a schematic illustration of an exemplary robotic surgical system configured to releasably receive the surgical instrument of FIG. 1.

Referring to FIGS. 1 and 2, a surgical instrument 10 provided in accordance with the present disclosure generally includes a housing 20, a shaft 30 extending distally from housing 20, an end effector assembly 40 extending distally from shaft 30, and an actuation assembly 100 disposed within housing 20 and operably associated with shaft 30 and end effector assembly 40. Instrument 10 is detailed herein as an articulating electrosurgical forceps configured for use with a robotic surgical system, e.g., robotic surgical system 500 (FIG. 3). However, the aspects and features of instrument 10 provided in accordance with the present disclosure, detailed below, are equally applicable for use with other suitable surgical instruments (including non-robotic surgical instrument) and/or in other suitable surgical systems (including non-robotic surgical systems).

Housing 20 of instrument 10 includes first and second body portion 22a, 22b and a proximal face plate 24 (FIG. 2) that cooperate to enclose actuation assembly 100 therein. Proximal face plate 24 includes apertures defined therein through which inputs 110-140 of actuation assembly 100 extend. A pair of latch levers 26 (only one of which is illustrated in FIG. 1) extend outwardly from opposing sides of housing 20 and enables releasable engagement (directly or indirectly) of housing 20 with a robotic arm of a surgical system, e.g., robotic surgical system 500 (FIG. 3). An aperture 28 defined through housing 20 permits thumbwheel 440 to extend therethrough to enable manual manipulation of thumbwheel 440 from the exterior of housing 20 to permit manual opening and closing of end effector assembly 40.

Shaft 30 of instrument 10 includes a distal segment 32, a proximal segment 34, and an articulating section 36 disposed between the distal and proximal segments 32, 34, respectively. Articulating section 36 includes one or more articulating components 37, e.g., links, joints, etc. A plurality of articulation cables 38, e.g., four (4) articulation cables, or other suitable actuators, extends through articulating section 36. More specifically, articulation cables 38 are operably coupled to distal segment 32 of shaft 30 at the distal ends thereof and extend proximally from distal segment 32 of shaft 30, through articulating section 36 of shaft 30 and proximal segment 34 of shaft 30, and into housing 20, wherein articulation cables 38 operably couple with an articulation assembly 200 of actuation assembly 100 to enable selective articulation of distal segment 32 (and, thus end effector assembly 40) relative to proximal segment 34 and housing 20, e.g., about at least two axes of articulation (yaw and pitch articulation, for example). Articulation cables 38 are arranged in a generally rectangular configuration, although other suitable configurations are also contemplated.

With respect to articulation of end effector assembly 40 relative to proximal segment 34 of shaft 30, actuation of articulation cables 38 is effected in pairs. More specifically, in order to pitch end effector assembly 40, the upper pair of cables 38 is actuated in a similar manner while the lower pair of cables 38 is actuated in a similar manner relative to one another but an opposite manner relative to the upper pair of cables 38. With respect to yaw articulation, the right pair of cables 38 is actuated in a similar manner while the left pair of cables 38 is actuated in a similar manner relative to one another but an opposite manner relative to the right pair of cables 38.

Distal segment 32 of shaft 30 defines a clevis portion of end effector assembly 40 that supports first and second jaw members 42, 44, respectively. Each jaw member 42, 44 includes a proximal extension portion 43*a*, 45*a* and a distal body portion 43*b*, 45*b*, respectively. Distal body portions 43*b*, 45*b* define opposed tissue-contacting surfaces 46, 48, respectively. Proximal extension portions 43*a*, 45*a* are pivotably coupled to one another about a pivot pin 50 and are operably coupled to one another via a cam drive mechanism 52 (described in greater detail below) to enable pivoting of jaw member 42 relative to jaw member 44 and distal segment 32 of shaft 30 between a spaced-apart position (e.g., an open position of end effector assembly 40) and an approximated position (e.g., a closed position of end effector assembly 40) for grasping tissue between tissue-contacting surfaces 46, 48. As an alternative to this unilateral configuration, a bilateral configuration may be provided whereby both jaw members 42, 44 are pivotable relative to one another and distal segment 32 of shaft 30.

Opposing longitudinally-extending channels (not shown) are defined through tissue-contacting surfaces 46, 48, respectively, of jaw members 42, 44. A translating cutting element (not shown) is provided and selectively advanceable to enable cutting of tissue grasped between tissue-contacting surfaces 46, 48 of jaw members 42, 44, respectively. A cutting drive assembly 300 (FIG. 2) of actuation assembly 100 provides for selective actuation of cutting element through channel(s) of jaw members 42, 44 to cut tissue grasped between tissue-contacting surfaces 46, 48. Cutting drive assembly 300 is operably coupled to third input 130 of actuation assembly 100 such that, upon receipt of appropriate rotational input into third input 130, cutting drive assembly 300 advances the cutting element between jaw members 42, 44 to cut tissue grasped between tissue-contacting surfaces 46, 48.

Continuing with reference to FIGS. 1 and 2, a drive rod (not shown) is operably coupled to end effector assembly 40 such that longitudinal actuation of drive rod pivots jaw member 42 relative to jaw member 44 between the spaced-apart and approximated positions, as detailed below. More specifically, urging drive rod proximally pivots jaw member 42 relative to jaw member 44 towards the approximated position while urging drive rod distally pivots jaw member 42 relative to jaw member 44 towards the spaced-apart position. However, the reverse configuration is also contemplated. Drive rod extends proximally from end effector assembly 40 through shaft 30 and into housing 20 wherein drive rod is operably coupled with a jaw drive assembly 400 of actuation assembly 100 to enable selective actuation of end effector assembly 40 to grasp tissue therebetween and apply a closure force within an appropriate jaw closure force range, e.g., in response to an appropriate rotational input into fourth input 140.

Tissue-contacting surfaces 46, 48 of jaw members 42, 44, respectively, are at least partially formed from an electrically conductive material and are energizable to different potentials to enable the conduction of electrical energy through tissue grasped therebetween, although tissue-contacting surfaces 46, 48 may alternatively be configured to supply any suitable energy, e.g., thermal, microwave, light, ultrasonic, etc., through tissue grasped therebetween for energy-based tissue treatment. Instrument 10 defines conductive pathways extending through housing 20 and shaft 30 to end effector assembly 40 that may include lead wires, contacts, and/or electrically-conductive components to enable electrical connection of tissue-contacting surfaces 46, 48 of jaw members 42, 44, respectively, to an energy source (not shown), e.g., an electrosurgical generator via an electrosurgical cable extending therebetween, for supplying energy to tissue-contacting surfaces 46, 48 to treat, e.g., seal, tissue grasped between tissue-contacting surfaces 46, 48.

Actuation assembly 100 is disposed within housing 20 and includes articulation assembly 200, cutting drive assembly 300, and jaw drive assembly 400. Articulation assembly 200 is operably coupled between first and second inputs 110, 120, respectively, of actuation assembly 100 and articulation cables 38 such that, upon receipt of appropriate rotational inputs into first and/or second inputs 110, 120, articulation assembly 200 manipulates cables 38 (FIG. 1) to articulate end effector assembly 40 in a desired direction, e.g., to pitch and/or yaw end effector assembly 40. Cutting drive assembly 300, as noted above, enables reciprocation of the cutting element between jaw members 42, 44 to cut tissue grasped between tissue-contacting surfaces 46, 48 in response to receipt of appropriate rotational input into third input 130. Jaw drive assembly 400 is operably coupled between fourth input 140 of actuation assembly 100 and drive rod such that, upon receipt of appropriate rotational input into fourth input 140, jaw drive assembly 400 pivots jaw members 42, 44 between the spaced-apart and approximated positions to grasp tissue therebetween and apply a closure force within an appropriate closure force range.

Actuation assembly 100 is configured to operably interface with a robotic surgical system 500 (FIG. 3) when instrument 10 is mounted on robotic surgical system 500 (FIG. 3), to enable robotic operation of actuation assembly 100 to provide the above-detailed functionality. That is, robotic surgical system 500 (FIG. 3) selectively provides rotational inputs to inputs 110-140 of actuation assembly 100 to articulate end effector assembly 40, grasp tissue between jaw members 42, 44, and/or cut tissue grasped between jaw members 42, 44. However, it is also contemplated that actuation assembly 100 be configured to interface with any other suitable surgical system, e.g., a manual surgical handle, a powered surgical handle, etc. For the purposes herein, robotic surgical system 500 (FIG. 3) is generally described.

Turning to FIG. 3, a schematic representation of a robotic surgical system 500 is configured for use in accordance with the present disclosure. Aspects and features of robotic surgical system 500 not germane to the understanding of the present disclosure are omitted to avoid obscuring the aspects and features of the present disclosure in unnecessary detail.

Robotic surgical system 500 generally includes a plurality of robot arms 502, 503; a control device 504; and an operating console 505 coupled with control device 504. Operating console 505 may include a display device 506, which may be set up in particular to display three-dimensional images; and manual input devices or handles 507, 508, by means of which a person, e.g., a surgeon, may be able to telemanipulate robot arms 502, 503 in a first operating mode. Robotic surgical system 500 may be configured for use on a patient 513 lying on a patient table 512 to be treated in a minimally invasive manner. Robotic surgical system 500 may further include a database 514, in particular coupled to control device 504, in which are stored, for example, pre-operative data from patient 513 and/or ana- tomical atlases.

Each of the robot arms 502, 503 may include a plurality of members, which are connected through joints, and a mounted device which may be, for example, a surgical tool "ST." One or more of the surgical tools "ST" may be instrument 10 (FIG. 1), thus providing such functionality on a robotic surgical system 500.

Robot arms 502, 503 may be driven by electric drives, e.g., motors, connected to control device 504. Control device 504, e.g., a computer, may be configured to activate the motors, in particular by means of a computer program, in such a way that robot arms 502, 503, and, thus, their mounted surgical tools "ST" execute a desired movement and/or function according to a corresponding input from manual input devices 507, 508, respectively. Control device 504 may also be configured in such a way that it regulates the movement of robot arms 502, 503 and/or of the motors.

Figure 4A:
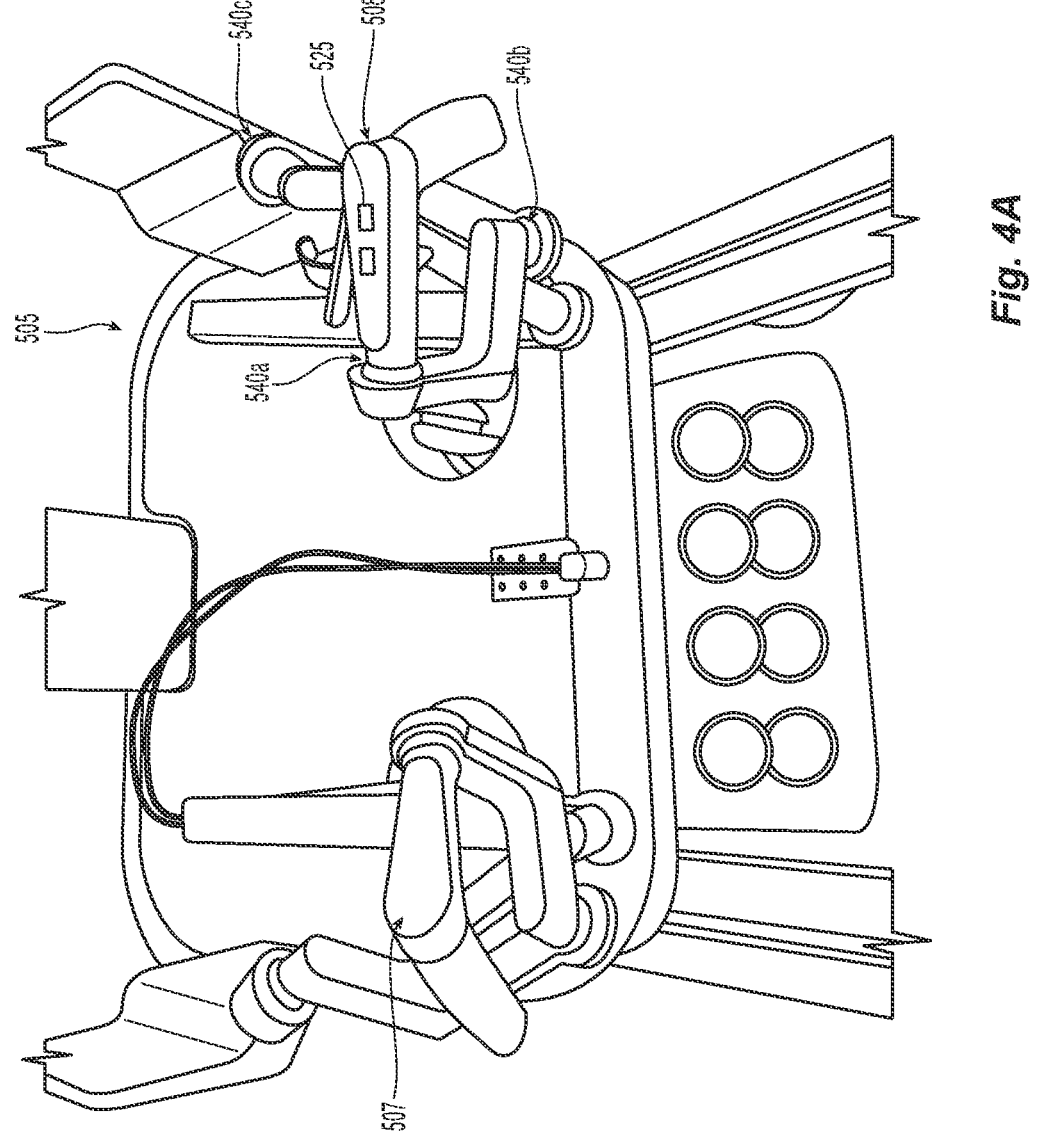
FIG. 4A is a top perspective view of the robotic surgical system of FIG. 3 showing a pair of operating handles for remotely controlling the surgical instrument.
Figure 4B:
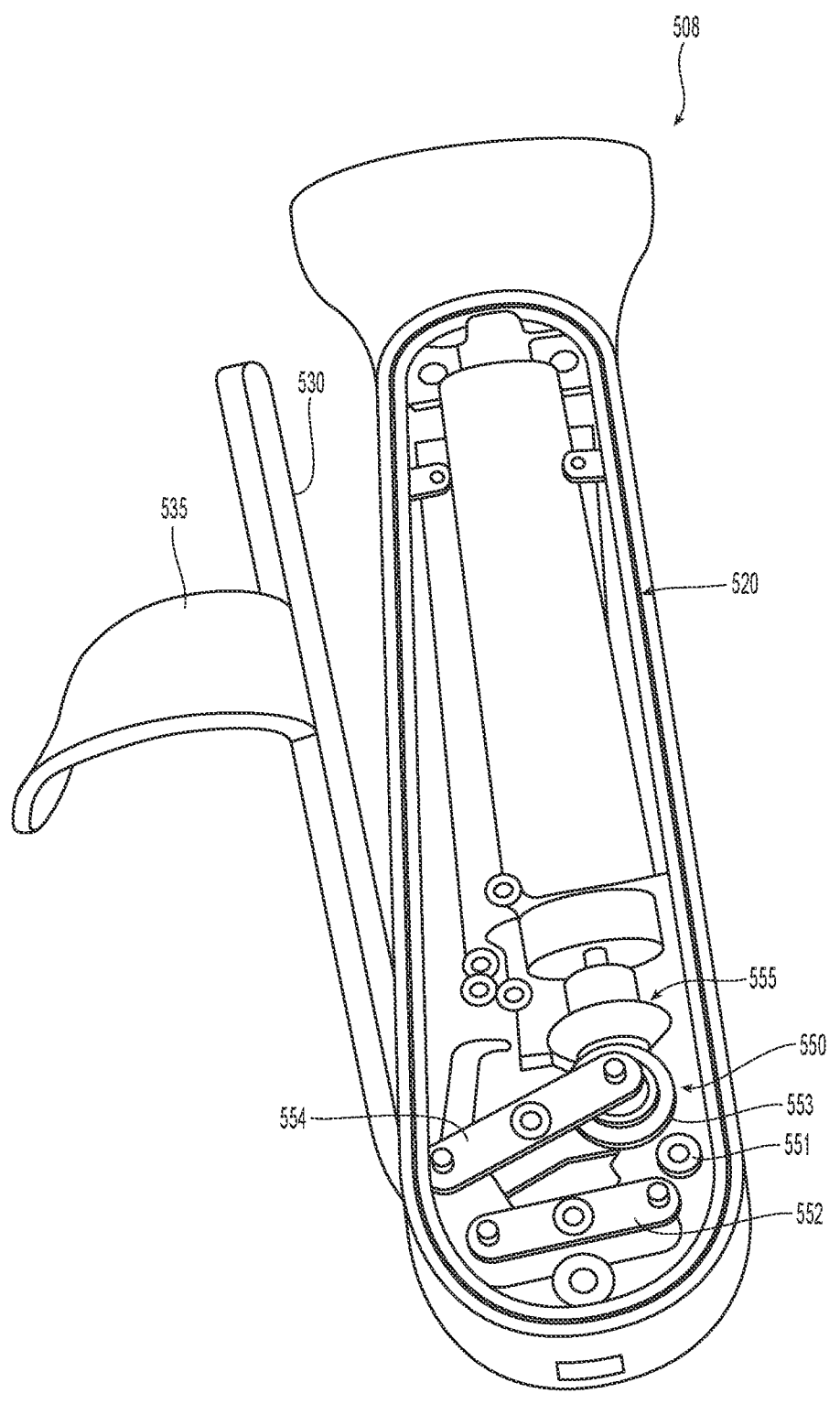
FIG. 4B is an enlarged view of one of the operating handles of the robotic surgical system of FIG. 4A.

Turning now to FIGS. 4A and 4B, portions of the oper- ating console 505 are depicted in more detail, namely, input devices or handles 507, 508. Each input device or handle 507, 508 includes similar components and, as such, only input device or handle 508 is depicted in FIG. 4B. Input device 508 includes a housing 520 defining a cavity 521 therein configured to house an actuation assembly 550 configured to communicate with one or more of the inputs 110-140 described in detail above. Housing 520 may be coupled to one or more gimbal mechanisms 540a-540c to control the extension, rotation, articulation, et. al. of the end effector assembly 40 as described above. Details relating to the various types of gimbal mechanisms that may be utilized for this purpose are disclosure in U.S. patent application Ser. No. 16/306,420, filed Nov. 30, 2018 entitled CONTROL ARM ASSEMBLIES FOR ROBOTIC SURGICAL SYS- TEMS, the entire contents of which are incorporated by reference herein.

Actuation assembly 550 is operatively coupled to a lever 530 which, upon actuation thereof relative to housing 520, opens and closes jaw members 42, 44 of end effector assembly 40. More particularly, lever 530 couples to a series of components, e.g., links, couplers, and/or actuators 551- 555, configured for communication with input 140 for controlling the closure of jaw members 42, 44 relative to one another as described above. Although depicted as a series of links, couplers and/or actuators 551-555, any type of mechanical or electromechanical arrangement is contem- plated. Moreover, and as explained below, actuation of lever 530 relative to the actuation of the jaw members 42, 44 may be linear 1:1, non-linear 1:2 or variable during the entire range of movement or stroke of the lever 530.

Lever 530 includes a finger support 535 which is config- ured to facilitate relative movement of the lever 530 to the housing 520. More particularly, finger support 535 may be cuff-like to envelop one or more fingers of the user to promote retraction of the lever 530 away from the housing 520 and facilitate rotation of the housing about one or more of the above-identified gimbal mechanisms 540a-540c.

As mentioned above, during robotic surgery involving the sealing of vessels or tissue, it is important that the surgeon adequately control the pressure between the jaw members 42, 44 both when grasping and manipulating tissue and when clamping on a vessel or tissue to create a seal. As can be appreciated, the pressure between jaw members 42, 44 when delicately grasping and manipulating vessels or tissue is significantly less than when sealing vessels or tissue. The various above-mentioned actuation assemblies, levers, gears, linkages, and springs discussed above all work in concert to facilitate actuation of the jaw members 42, 44 from the remote input devices or handles 507, 508. Typi- cally, movement of the lever 530 a fixed distance relative to housing 520 will actuate the jaw members 42, 44 under the same force irrespective of the size of the vessel or tissue.

For example, with robotic vessel sealing devices such as those described above, the actuation of the jaw members 42, 44 is controlled through motor rotations which are mapped to the actuation lever 530. Since the forces required to generate a proper seal are typically on the order of 100 psi or greater, the software maps the relative movement of the surgeon's fingers and lever 530 to the housing 520 and correlates this relative movement to the jaw members 42, 44. Various software algorithms are utilized for this purpose. As a result, very little force is required to move the lever 530 relative to the housing 520 via the surgeon's fingers to generate the proper pressure for sealing tissue. This also helps to offset surgical fatigue. However, since the robotic sealer is designed to generate sealing pressures at the jaw members 42, 44 with far less comparative forces at the lever 530, in some instances too much pressure, e.g., pressures associated with sealing tissue, may be applied to a vessel or tissue bundle when the surgeon's intention is to simply grasp, manipulate or cut tissue.

Figure 5A:
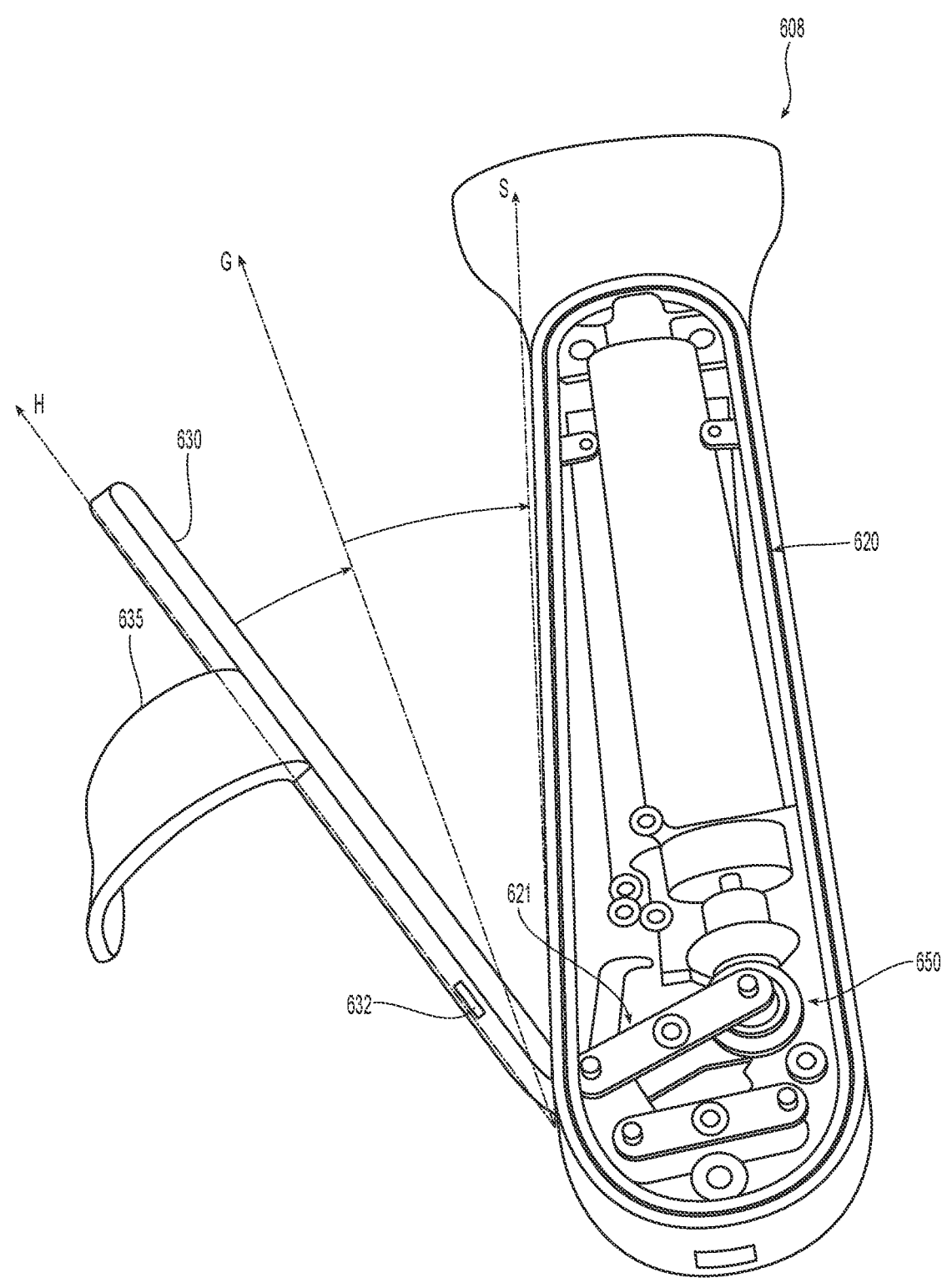
FIG. 5A is an enlarged view of one of the operating handles in accordance with another embodiment of the present disclosure.
Figure 5B:
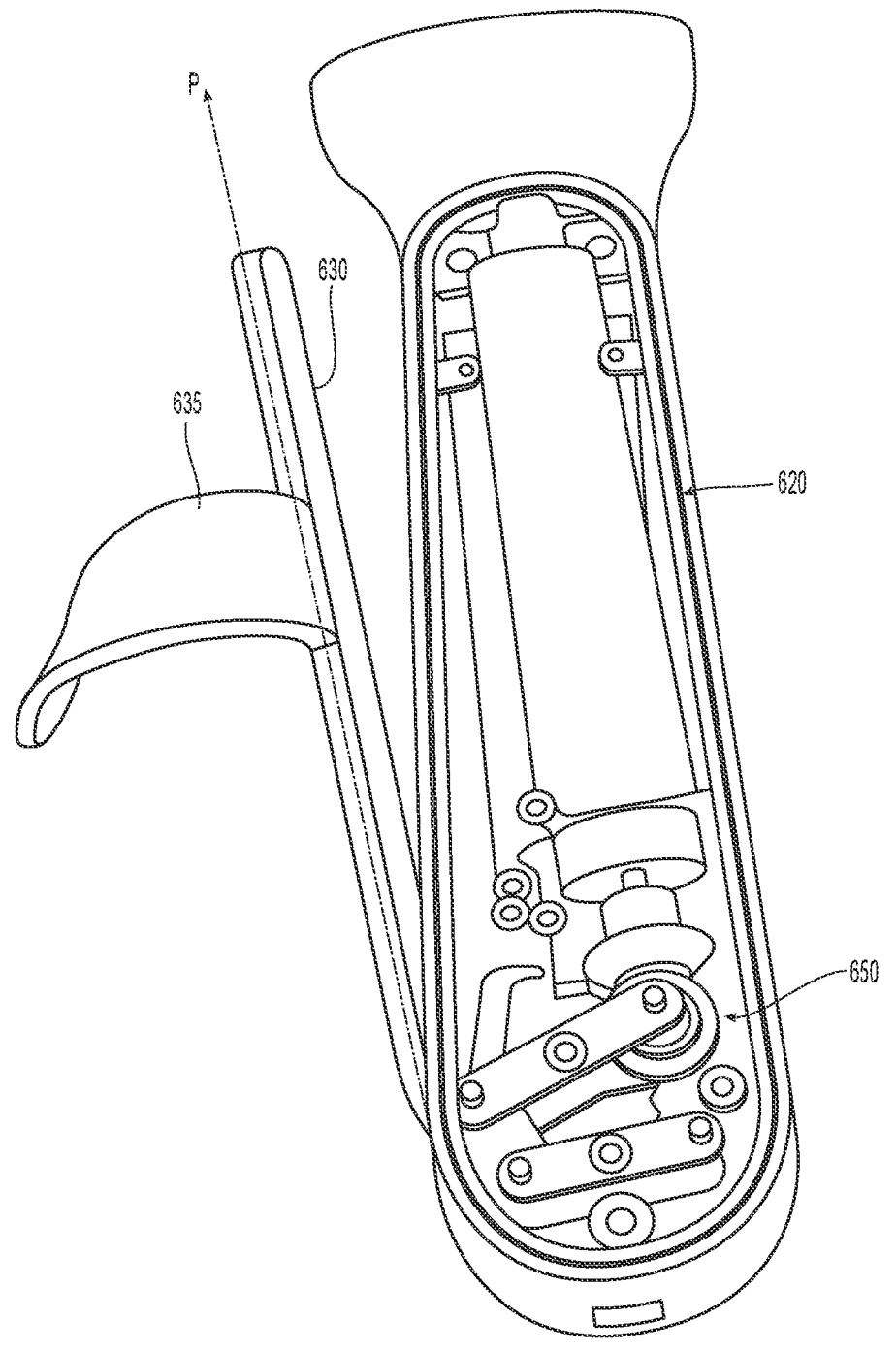
FIG. 5B is an enlarged view of one of the operating handles in accordance with yet another embodiment of the present disclosure.

FIGS. 5A and 5B show one embodiment of an input device or handle 608 in accordance with the present disclo- sure which includes a variable-force lever 630 configured to allow grasping, manipulation and cutting when moved to a first position and configured to generate the requisite pres- sure between the jaw members 42, 44 when moved to a second position for sealing vessels and tissue. Input device 608 includes a variable force lever 630 having various mechanical, electromechanical or other features (e.g., soft- ware) that are configured regulate and correlate the relative motion of the lever 630 with the motion of the jaw members 42, 44. More particularly and as shown in FIG. 5A, initial movement of lever 630 from an unactuated position or home position "H" towards a grasp position "G" actuates one or both of the jaw members 42, 44 to grasp a vessel or tissue with a first pressure known to avoid structural damage to sensitive tissue. Pressures in the range of about 0.01 Kg/cm$^2$ to about 2 kg/cm$^2$ are contemplated. Pressures up to and including the lower range of the below-identified sealing pressure range are also contemplated. The force on the handle may be linear, e.g., the same amount of force through the entire range of motion from position "H" to position "G", or may be non-linear, e.g., the amount of force varies within the above-identified range through the range of motion from position "H" to position "G".

As can be appreciated, the surgeon can remotely actuate the jaw members 42, 44 to manipulate, grasp and cut (e.g., without a seal if applicable) vessels and tissue by continually moving the lever 630 between positions "H" and position "G" without any concern of applying too much force to vessels or tissue. Vessels or tissue may also be dissected when moving the lever from position "G" to position "H", e.g., poke and spread dissection.

Once the vessel or tissue is properly grasped, the surgeon may opt to seal the vessel or tissue between the jaw members 42, 44. In this instance the surgeon moves the lever 630 closer the housing 620, e.g., from position "G" to position "S" which, in turn, generates additional forces between the jaw members 42, 44 to enable sealing once the robotic sealer 10 is activated via one or more activation buttons 525 (FIG. 4A). Forces within the range of about 3 kg/cm$^2$ to about 16 kg/cm$^2$ are contemplated for sealing purposes. A switch or other safety feature 632 may be operably associated with the lever 630 and employed to switch the lever 630 between modes or reposition or add mechanical or electromechanical components 650 to change the applied forces from the lever 630 to the jaw members 42, 44. The components 650 may be disposed in a cavity 621 defined in the housing 620 and may be arranged to provide resistance to the lever 630 correlating to the resistance of the tissue disposed between the jaw members 42, 44.

Lever 630 includes a finger support 635 which is configured to facilitate relative movement of the lever 630 to the housing 620. More particularly, finger support 635 may be cuff-like to envelop one or more fingers of the user to the promote retraction of the lever 630 away from the housing 620 and facilitate rotation of the housing about one or more of the above-identified gimbal mechanisms, e.g., gimbal mechanisms 540a-540c of FIG. 4A.

Figure 6:
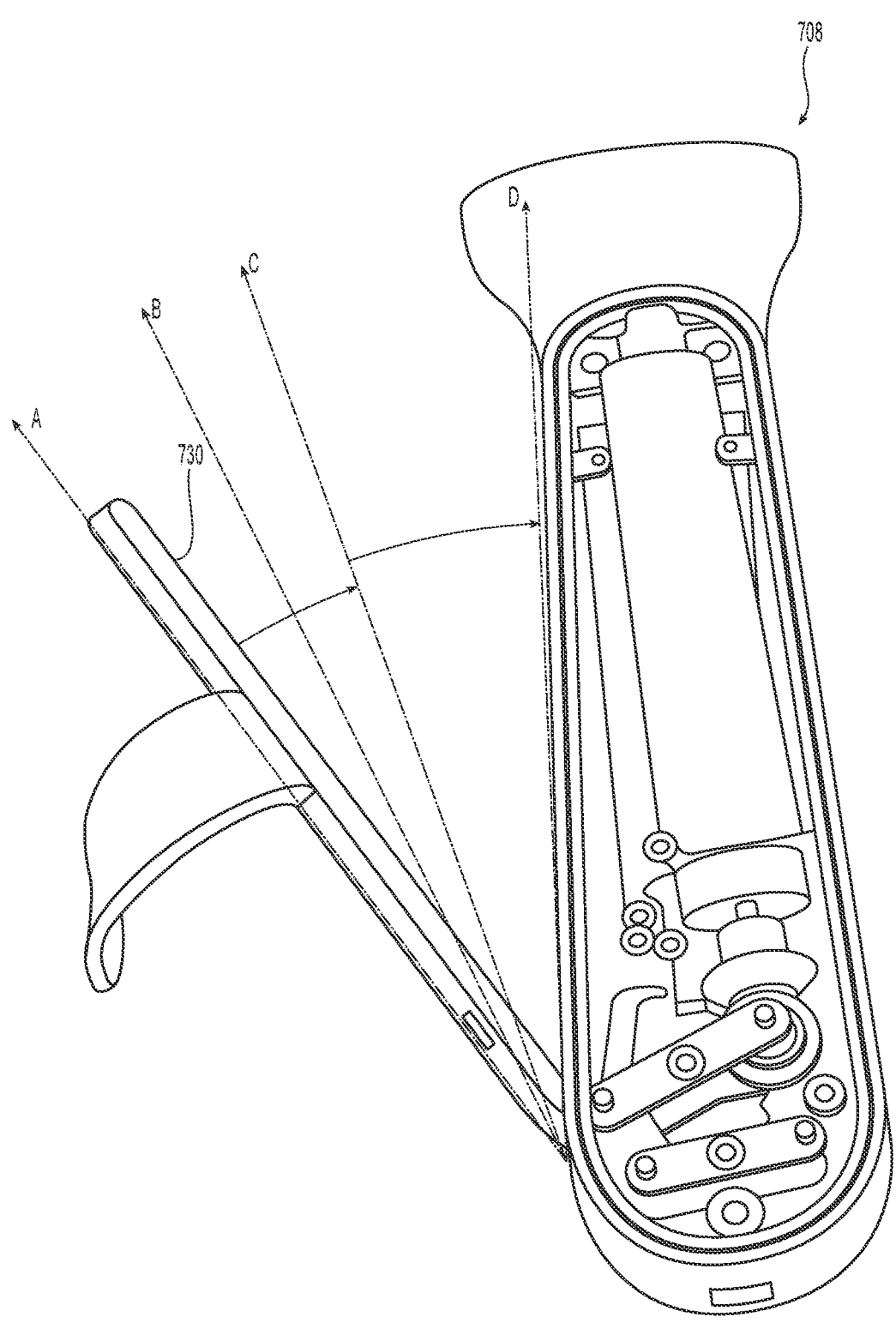
FIG. 6 is an enlarged view of the operating handles in accordance with still another embodiment of the present disclosure

Turning briefly to FIG. 6, another embodiment of a handle 708 is envisioned which adjusts the haptic feedback of the lever 730 based on empirical data such that each lever stroke continues from a fully open position, through a typical grasping position and to a position for sealing tissue. More particularly, point "A" position on the lever 730 indicates a fully open position wherein the jaw members 42, 44 are fully open to orient tissue therebetween. Between point "A" and point "B", with the lever 730 starting to close, there is only a slight haptic force associated with the lever 730, e.g., very little resistance on the lever 730. Point "B" may be customizable depending on the particular instrument or based on empirical data, e.g., point "B" is configured on the lever 730 as the point between a large vessel disposed within the jaws 42, 44 and nothing in the jaws 42, 44. In other instances, point "B" may be customizable based on the feedback from sensors or torque.

Between point "B" and point "C" the lever 730 begins to compress a spring (or some other pressure control mechanism (not shown)) which will provide direct haptic feedback to the surgeon regarding pressure between jaw members 42, 44. The lever 730 and spring relationship may be linear or exponential or may be a combination, e.g., initially linear and then exponential. In embodiments, moving the lever between points "B" and "C" may induce a pressure within the above-identified sealing range and the surgeon may opt to seal tissue based on perceived haptic feedback within this stroke range. Alternatively, a point "C" may be included within the lever stroke that definitively identifies that the jaw pressure is within the sealing range. Any further movement of the lever 730 does not increase the pressure between the jaw members 42, 44, e.g., the pressure is offloaded by the spring (or some other pressure control mechanism (not shown)) to not over-compress the tissue. Point "D" may be included as a bottom out point of the lever 730.

It is contemplated that any combination of mechanical components, electromechanical components, software, etc. may be utilized to map or correlate the various positions of the lever 630 to the input 140 which, in turn, controls the relative movement of the jaw members 42, 44. Again, the relationship of the lever 630 to the movement of the jaw members 42, 44 may be linear or non-linear depending upon a particular purpose. Moreover, the lever 630 may be coupled to one or more mechanical, electromechanical components, e.g., components 551-555 (FIG. 4B), or software, that are configured to vary the actuation force (either linearly or non-linearly) as the lever 630 is actuated relative to housing 620 simulating the "feel" of the jaw members 42, 44 grasping, manipulating or sealing vessels or tissue. In other instances, a visual signal (e.g., a series of LEDs or the like or varying colors) or audible tone (generally represented by component 545 of robotic system 500 (FIG. 3)) may be used to represent the amount of pressure being applied to the vessel or tissue during the relative movement of the level 630.

As mentioned above, the force on the lever 630 is correlated to the closure pressure between the jaw members 42, 44 based on the position of the lever 630 relative to the housing 620. In embodiments, the resistance on the lever 630 may be related to the internal mechanical or electromechanical components 551-555 (FIG. 4B) or may be based on software associated with one or more of the components or input 140. In this instance, there is no reliance on a sensor providing feedback to the components 551-555 or software to alter or otherwise effect the resistance on the level 630.

As mentioned above, various visual or audible feedback 545 may be conveyed to the surgeon relating to the amount of pressure between the jaw members 42, 44. The feedback may be as simple as a "SAFE" signal for manipulation, e.g., green light, safe tone, or may be metered in relation to the amount of pressure being applied to tissue and when a pressure is being applied to warrant sealing, e.g., "SEAL" signal. The metering of the feedback either visually or audibly provides ample feedback to the surgeon when he/she is approaching unintended pressures between the jaw members 42, 44.

In one embodiment according to the present disclosure, the handle 608, robotic controller 505, robotic sealer 10, or the software associated with one or more of the foregoing may be configured to switch the relative motion of the lever 630 and the resulting closure pressure associated with the jaw members 42, 44 based on user selection. More particularly, in a first instance or with a first user selection, e.g., grasping, manipulation, cutting or dissection mode, actuation of the lever 630 may ramp from the jaw members 42, 44 being spaced from one another (e.g., zero closure force between jaw members 42, 44) to a correlating pressure between the jaw members 42, 44 within a range of about 0.1 kg/cm$^2$ to about 2 kg/cm$^2$. Other pressure ranges for grasping, manipulation, cutting or dissection are envisioned. The relationship of the lever 630 force to the jaw member 42, 44 closure pressure may be linear or non-linear within this range.

In a next instance or with a second or different user selection, e.g., sealing, actuation of the lever 630 may ramp from the jaw members 42, 44 being spaced from one another to a correlating pressure between the jaw members 42, 44 within a range of about 3 kg/cm$^2$ to about 16 kg/cm$^2$. Again, the relationship of the lever 630 force to the jaw member 42, 44 sealing pressure may be linear or non-linear within this range. Various audible or visual safety measures 545 may be employed with the handle 608 or robotic surgical system 500 to alert the user of the current disposition of the lever 630 and which pressure will be applied to the jaw members 42, 44 upon actuation thereof.

Various safety measures may be employed using one or more mechanical, electromechanical or software that would only allow a sealing pressure to be delivered when energy is being applied. For example, a slight delay may be programmed into the control software to delay activation of electrosurgical energy until a proper jaw pressure is applied between the jaw members 42, 44 via the lever 630.

It will be understood that various modifications may be made to the aspects and features disclosed herein. Therefore, the above description should not be construed as limiting, but merely as exemplifications of various aspects and features. Those skilled in the art will envision other modifications within the scope and spirit of the claims appended thereto.

What is claimed is:

1. A robotic surgical system, comprising:
an electrosurgical instrument, including:
an instrument housing having a shaft extending therefrom;
an end effector assembly disposed at a distal end of the shaft, the end effector assembly including first and second jaw members at least one of which is movable relative to the other to grasp tissue; and
an input operably coupled to the instrument housing and configured to move the at least one of the jaw members; and
at least one handle remotely disposed relative to the instrument housing and configured to communicate with the input for controlling the jaw members, the at least one handle including:
a housing having a lever operably coupled thereto, the lever, in turn, configured to cooperate with the input to control the movement of the at least one of the jaw members,
wherein the lever is movable from a home position wherein the lever is spaced relative to the housing and the jaw members are disposed in a spaced apart position to a grasp position wherein the lever is closer to the housing to impart movement of the jaw members to grasp tissue with a grasping pressure between the jaw members to inhibit damage to tissue,
wherein the lever is movable from the grasp position to a seal position wherein the lever is closer to the housing to impart movement of the jaw members to grasp tissue with a sealing pressure between the jaw members to seal tissue between the jaw members upon activation of electrosurgical energy, and
wherein the sealing pressure is maintained in response to movement of the lever from the seal position to an end position of the lever wherein the lever is closer to the housing.

2. The robotic surgical system according to claim 1, wherein the housing of the at least one handle includes a cavity defined therein configured to house one or more components therein configured to operably connect to the input such that movement of the lever relative to the housing moves the at least one of the jaw members.

3. The robotic surgical system according to claim 1, wherein a correlation of movement of the lever and the at least one of the jaw members is non-linear.

4. The robotic surgical system according to claim 2, wherein the combination of components disposed in the cavity correlate the position of the lever to a pressure applied to tissue grasped between the jaw members.

5. The robotic surgical system according to claim 2, wherein the combination of components disposed in the cavity includes at least one of a gear, a linkage, or a spring.

6. A robotic surgical system, comprising:
an electrosurgical instrument, including:
an instrument housing having a shaft extending therefrom;
an end effector assembly disposed at a distal end of the shaft, the end effector assembly including first and second jaw members at least one of which is movable relative to the other to grasp tissue; and

an input operably coupled to the instrument housing and configured to move the at least one of the jaw members; and
at least one handle remotely disposed relative to the instrument housing and configured to communicate with the input for controlling the jaw members, the at least one handle including:
a housing having a lever operably coupled thereto, the lever, upon movement thereof, cooperating with the input to impart movement of the at least one of the jaw members, wherein initial movement of the lever towards the housing from an unactuated position to a first position imparts movement to the at least one of the jaw members to grasp tissue with a grasping pressure to inhibit damage to tissue, wherein subsequent movement of the lever towards the housing beyond the first position imparts movement to the at least one of the jaw members to grasp tissue with a sealing pressure to seal tissue between the jaw members upon activation of electrosurgical energy, and wherein, once the sealing pressure is reached, the sealing pressure is maintained in response to further movement of the lever towards the housing.

7. The robotic surgical system according to claim 6, wherein the housing of the at least one handle includes a cavity defined therein configured to house one or more components therein configured to operably connect to the input such that movement of the lever relative to the housing moves the at least one of the jaw members.

8. The robotic surgical system according to claim 6, wherein a correlation of movement of the lever and the at least one of the jaw members is non-linear.

9. The robotic surgical system according to claim 7, wherein the combination of components disposed in the cavity correlate the position of the lever to a pressure applied to tissue grasped between the jaw members.

10. The robotic surgical system according to claim 9, wherein the combination of components disposed in the cavity includes at least one of a gear, a linkage, or a spring.

11. The robotic surgical system according to claim 6, further comprising at least one of a tactile, visual or audible indicator operably associated with the lever configured to alert the user when the lever is moved beyond the first position.

12. A robotic surgical system, comprising:
an electrosurgical instrument, including:
an instrument housing having a shaft extending therefrom;
an end effector assembly disposed at a distal end of the shaft, the end effector assembly including first and second jaw members at least one of which is movable relative to the other to grasp tissue; and
an input operably coupled to the instrument housing and configured to move the at least one of the jaw members; and
at least one handle remotely disposed relative to the instrument housing and configured to communicate with the input for controlling the jaw members, the at least one handle including:
a housing having a lever operably coupled thereto, the lever movable relative to the housing between a first lever position and a second lever position; and
a switch operably disposed on at least one of the lever or the housing, the switch movable between a first switch position and a second switch position, wherein:

with the switch disposed in the first switch position, movement of the lever from the first lever position to the second lever position cooperates with the input to impart movement to the jaw members to grasp tissue with a grasping pressure within a grasping pressure range to inhibit damage to tissue, and with the switch disposed in the second switch position, movement of the lever from the first lever position to the second lever position cooperates with the input to impart movement to the jaw members to grasp tissue with a sealing pressure within a sealing pressure range greater than the grasping pressure range to enable sealing of tissue between the jaw members upon activation of electrosurgical energy.

13. The robotic surgical system according to claim 12, wherein movement of the switch to the second switch position configures the jaw members for electrosurgical activation.

14. The robotic surgical system according to claim 12, wherein when the switch is disposed in the first switch position, electrosurgical energy is deactivated.

15. The robotic surgical system according to claim 12, further comprising at least one of a tactile, visual or audible indicator of a applied to tissue grasped between the jaw members.

* * * * *